United States Patent
Pastore et al.

(10) Patent No.: US 7,761,151 B2
(45) Date of Patent: Jul. 20, 2010

(54) INTERMITTENT HIGH-ENERGY CARDIAC STIMULATION FOR THERAPEUTIC EFFECT

(75) Inventors: Joseph M. Pastore, Woodbury, MN (US); Imad Libbus, St. Paul, MN (US); Andrew P. Kramer, Stillwater, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 231 days.

(21) Appl. No.: 11/466,679

(22) Filed: Aug. 23, 2006

(65) Prior Publication Data

US 2008/0051842 A1  Feb. 28, 2008

(51) Int. Cl.
*A61N 1/00* (2006.01)
(52) U.S. Cl. .............................. 607/4; 607/2
(58) Field of Classification Search ............... 607/4–28, 607/2
See application file for complete search history.

(56) References Cited

U.S. PATENT DOCUMENTS

| 5,836,971 | A | 11/1998 | Starkweather |
| 6,292,693 | B1 | 9/2001 | Darvish et al. |
| 6,363,279 | B1 * | 3/2002 | Ben-Haim et al. ............ 607/9 |
| 7,277,761 | B2 | 10/2007 | Shelchuk |
| 2003/0125778 | A1 * | 7/2003 | Cho et al. ..................... 607/27 |
| 2003/0195579 | A1 * | 10/2003 | Bradley et al. ................ 607/27 |
| 2003/0204209 | A1 | 10/2003 | Burnes et al. |
| 2004/0064162 | A1 * | 4/2004 | Manrodt et al. ............... 607/28 |

FOREIGN PATENT DOCUMENTS

WO  WO-2008/024312 A2  2/2008

OTHER PUBLICATIONS

PCT Application No. PCT/US2007/018416, Invitation to Pay Additional Fees and Partial International Search Report mailed Feb. 21, 2008 (6 pgs.).
Adamopoulos, S., "Effects of Pulsed β-Stimulant Therapy on β-adrenoceptors and Chronotropic Responsiveness in Chronic Heart Failure.", *Lancet*, 345(8946), (1995), 344-349.
Blinks, J. R., "Field Stimulation as a Means of Effecting the Graded Release of Autonomic Transmitters in Isolated Heart Muscle", *The Journal of Pharmacology and Experimental Therapy*, 151(2), (1966), 221-235.
Coats, A. J., "Controlled Trial of Physical Training in Chronic Heart Failure. Exercise Performance, Hemodynamics, Ventilation, and Autonomic Function.", *Circulation*, 85(6), (1992), 2119-2131.

(Continued)

*Primary Examiner*—Scott M Getzow
(74) *Attorney, Agent, or Firm*—Schwegman, Lundberg & Woessner, P.A.

(57) ABSTRACT

A device and method for delivering high-energy electrical stimulation to the heart in order to improve cardiac function in heart failure patients. The high-energy stimulation mimics the effects of exercise and improves symptoms even in patients who are exercise intolerant. The high-energy stimulation may be delivered on an intermittent basis either as pacing pulses in accordance with a programmed pacing mode and with a higher pacing pulse energy than used for conventional pacing or as low energy shock pulses.

25 Claims, 3 Drawing Sheets

OTHER PUBLICATIONS

Leier, C. V., "Drug-induced Conditioning in Congestive Heart Failure.", *Circulation*, 65(7), (1982),1382-1387.

Liang, C.-S., "Conditioning Effects of Chronic Infusions of Dobutamine. Comparison with Exercise Training.", *Journal of Clinical Investigation*, 64(2), (1979), 613-619.

Liang, C. S., "Sustained Improvement of Cardiac Function in Patients With Congestive Heart Failure After Short-Term Infusion of Dobutamine", *Circulation*, 69(1), (1984), 113-119.

Olson, R. D., et al., "Quantification of the Voltage-Response Relationship Between Punctate and Field Electrical Stimulation and the Function of Isolated Rat Left Atria and Papillary Muscles", *Journal of Pharmacological and Toxicological Methods*, 34(4), 1995, 225-230.

Sabbah, H. N., et al., "Chronic Therapy With Non-Excitatory Cardiac Contractility Modulation Electric Signals Improves Left Ventricular Function, Reduces Myocardial Oxygen Consumption and Increases Myocardial Mechanical Efficiency", (AB22-5), *Heart Rhythm*, 2(5)(Suppl.), (May 2005), p. S44.

Siegel, R. M., et al., "Do Elderly Patients with Chronic Left Ventricular Systolic Dysfunction Benefit from Aerobic Training and Supervised Cardiac Rehabilitation?", (Abstract No. 409), *Journal of Cardiac Failure*, 11(6)(Suppl.), (Abstracts from the 9th Annual Meeting, Heart Failure Society of America), (Aug. 2005), S198-S199.

Tohmeh, J. F., "Biphasic Adrenergic Modulation of β-Adrenergic Receptors in Man. Agonist-Induced Early Increment and Late Decrement in β-Adrenergic Receptor Number", *J Clin Invest.*, 65(4), (1980), 836-840.

"International Application Serial No. PCT/US2007/018416, International Search Report mailed Jun. 9, 2008", 6 pgs.

"International Application Serial No. PCT/US2007/018416, Written Opinion mailed Jun. 9, 2008", 8 pgs.

* cited by examiner

INTERMITTENT HIGH-ENERGY CARDIAC STIMULATION FOR THERAPEUTIC EFFECT

FIELD OF THE INVENTION

This invention pertains to apparatus and methods for the treatment of heart disease and to devices providing electro-stimulation to the heart such as cardiac pacemakers.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Heart failure can be treated with a drug regimen designed to augment cardiac function and/or relieve congestive symptoms or by pacing therapy. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

It has long been known that the heart muscle responds favorably to exercise so as to result in greater pumping efficacy. Studies have shown that HF patients can improve their cardiac function and achieve some relief from symptoms with regular exercise. Many HF patients, however, are either debilitated and cannot exercise or do not tolerate exercise well enough to exercise effectively.

DETAILED DESCRIPTION

Clinical studies have shown that heart failure patients who follow a regular (e.g. 20 min/day, 3 times a week) exercise regimen have symptomatic improvement compared to those who are sedentary. However, not all heart failure patients can exercise due to their cardiac disease or other debilitating conditions. An alternative method to improve symptoms is to have regular, intermittent release of neurotransmitters. Short durations (e.g. 30 min/day, 3-4 times per week) of enhanced neurotransmitter release (e.g., dobutamine) have been shown clinically to provide improvement in heart failure symptoms similar to the effects of exercise. Studies have also shown that local release of sympathetic and parasympathetic neurotransmitters is elicited by high-energy stimulation to cardiac tissue. Therefore, short durations of high-energy stimulation may improve heart failure symptoms by appropriately timed release of neurotransmitters. This disclosure describes methods and devices that use short durations of high-energy stimulation to provide protection from heart failure development and/or attenuation/reversal of cardiac disease progression.

As described below, a device for delivering such intermittent high-energy stimulation may be a device with the capability of also delivering bradycardia pacing, CRT, cardioversion/defibrillation shocks, and/or neural stimulation (e.g., vagal nerve stimulation). The device may be equipped with leads for placement in the ventricle and/or atrium with the capability to deliver high-energy pulses for a prescribed amount of time per day (e.g. 30 min). The time when therapy delivery is started may be random (once per day at a random time), at a specific time each day, or triggered by a specific event (e.g. when the patient falls asleep, the patient wakes up, the activity level falls below a certain threshold). The high-energy therapy may be delivered as a high-energy (e.g. five times diastolic pacing threshold) pacing pulse delivered directly through a pacing lead, or a low-energy (e.g. 0.5 J) shock below the pain threshold and which is delivered through a shocking coil. The pacing pulses or shocks can be delivered from one or multiple leads, either simultaneously or with timing offsets between them.

1. Exemplar Cardiac Device

Figure 1:
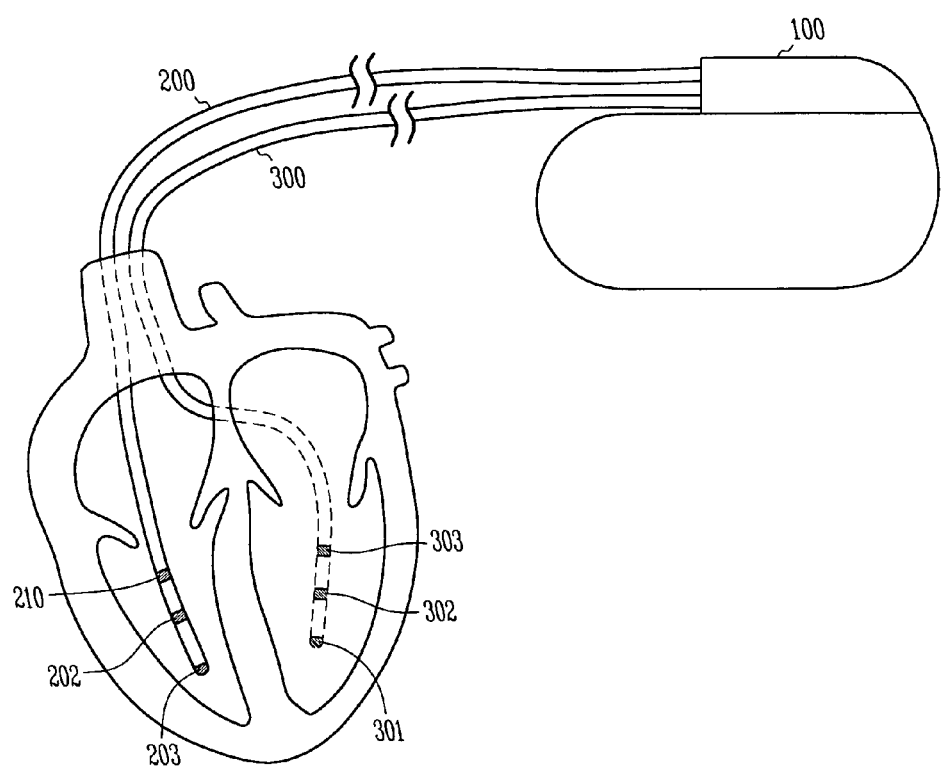
FIG. 1 illustrates the physical configuration of an exemplary cardiac device.

Cardiac rhythm management devices such as pacemakers and implantable cardioverter/defibrillators (ICD's) are usually implanted subcutaneously on a patient's chest and have leads threaded intravenously into the heart to connect the device to electrodes used for sensing and stimulation. In the case of a pacemaker, a programmable electronic controller causes pacing pulses to be output in response to lapsed time intervals and sensed intrinsic electrical activity (i.e., intrinsic heart beats not as a result of a pacing pulse) to treat bradycardia, tachycardia, or conduction disorders. In the case of an ICD, the controller causes delivery of a cardioversion/defibrillation shock in response to the detection of a tachyarrhythmia. These devices sense intrinsic cardiac electrical activity by means of internal electrodes disposed near the chamber to be sensed, where depolarization wave associated with an intrinsic contraction of the atria or ventricles that is detected is referred to as an atrial sense or ventricular sense, respectively. In order to cause a contraction in the absence of an intrinsic beat, a pacing pulse (either an atrial pace or a ventricular pace) with energy above a certain pacing threshold is delivered to the chamber during a non-refractory period, referred to as an excitatory pacing pulse. Cardiac rhythm management devices may utilize one or more multi-electrode leads each having a plurality of electrodes in order to excite different myocardial sites. FIG. 1 shows an exemplary device 100 having two leads 200 and 300, each of which is a multi-electrode lead having electrodes 201-203 and 301-303, respectively. The electrodes 201-203 are disposed in the right ventricle in order to excite right ventricular or septal regions, while the electrodes 301-303 are disposed in the coronary sinus in order to excite regions of the left ventricle. Other devices may use one or more single-electrode leads. As explained below, once the device and leads are implanted, the pacing and/or sensing channels of the device may be configured with selected ones of the multiple electrodes in order to selectively pace or sense a particular myocardial site.

Figure 2:
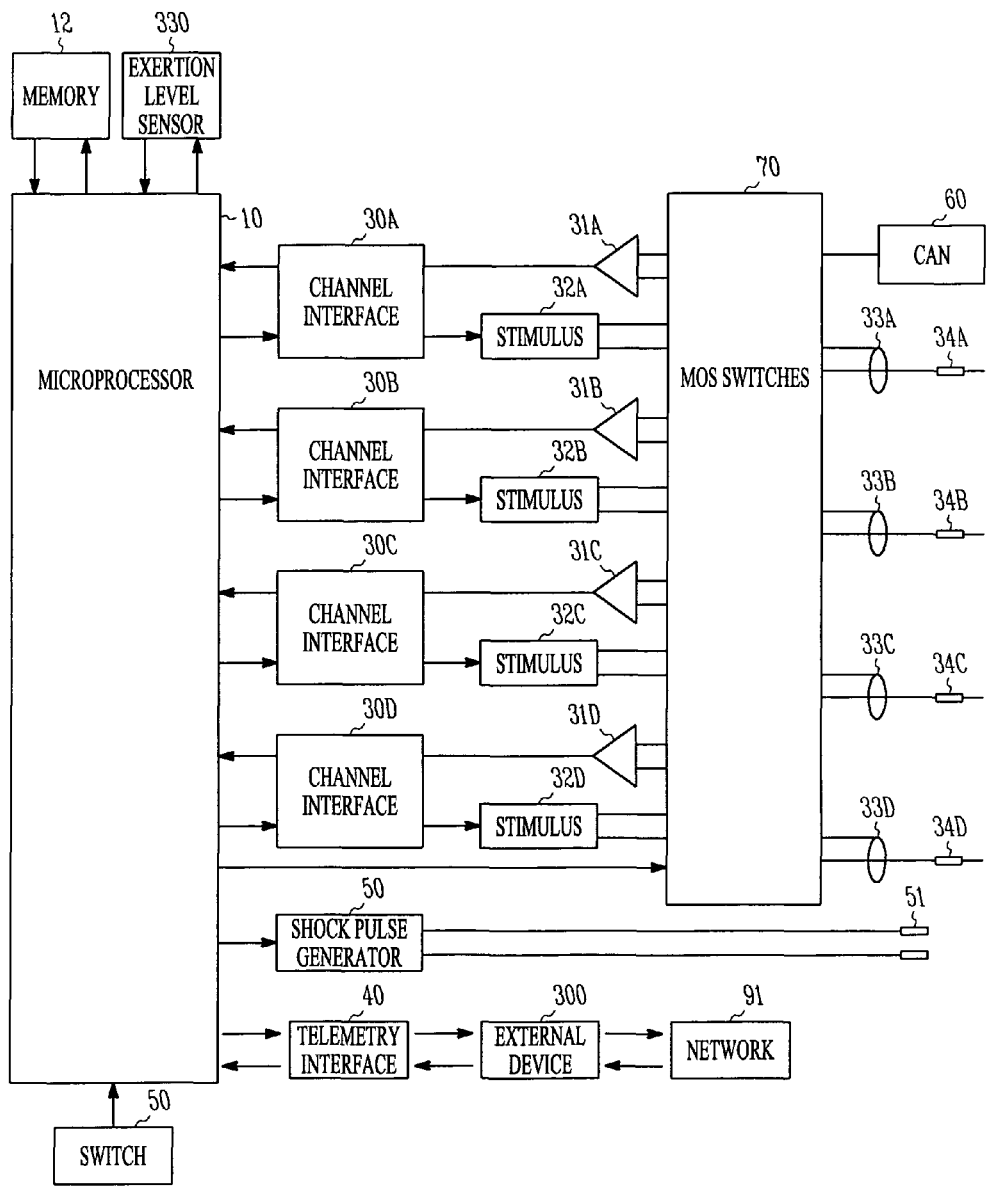
FIG. 2 is a block diagram of an exemplary cardiac device.

FIG. 2 shows a system diagram of a microprocessor-based cardiac rhythm management device such as illustrated in FIG. 1 that is suitable for practicing the present invention. The controller of the device includes a microprocessor 10 which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Not shown in the figure are other circuitry components necessary for controller operation such as circuitry for supplying power and external clock signals.

The device is equipped with multiple electrodes each of which may be incorporated into a pacing and/or sensing channel. Shown in the figure are four exemplary sensing and pacing channels designated "a" through "d" comprising bipolar leads with ring electrodes 33a-d and tip electrodes 34a-d, sensing amplifiers 31a-d, pulse generators 32a-d, and channel interfaces 30a-d. Each channel thus includes a pacing channel made up of the pulse generator connected to the electrode and a sensing channel made up of the sense amplifier connected to the electrode. By appropriate placement of the electrode, a channel may be configured to sense and/or pace a particular atrial or ventricular site. The channel interfaces 30a-d communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude/width, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats and/or follow atrial paces. As described below, delivery of pacing pulses to one or more myocardial sites is one means for delivering intermittent high-energy stimulation for cardio-therapeutic effect.

The electrodes of each bipolar lead are connected via conductors within the lead to a MOS switching network 70 controlled by the microprocessor. The switching network is used to configure sensing channels by switching selected electrodes to the input of a sense amplifier in order to detect intrinsic cardiac activity and to configure pacing channels by switching selected electrodes to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. One or more pacing channels may also be configured, by appropriate lead placement and pulse energy settings, for delivering electrical stimulation to stimulate sympathetic and/or parasympathetic nerves. For example, a lead with a stimulation electrode may be placed in proximity to the vagus nerve in order to stimulate that nerve and increase parasympathetic activity. A shock pulse generator 50 is also interfaced to the controller that may be used for delivering a cardioversion/defibrillation shock via a pair of shock electrodes 51 to the atria or ventricles upon detection of a tachyarrhythmia. The shock electrodes may, for example, be the device housing together with a coil electrode disposed in a heart chamber. As described below, shocks may also be delivered at a lower energy than that used for defibrillation as one means for implementing intermittent high-energy stimulation for cardio-therapeutic effect. A magnetically or tactilely actuated switch 500 is also interfaced to the controller that allows the patient to initiate or cease high-energy stimulation.

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller also implements timers derived from external clock signals in order to keep track of time and implement real-time operations such as scheduled high-energy stimulation. An exertion level sensor 330 (e.g., an accelerometer, a minute ventilation sensor, or other sensor that measures a parameter related to metabolic demand) enables the controller to adapt the pacing rate in accordance with changes in the patient's physical activity. As described below, the exertion level sensor may also be used in scheduling delivery of intermittent high-energy stimulation. A telemetry interface 40 is provided which enables the controller to communicate with an external device 300 such as an external programmer via a wireless telemetry link. An external programmer is a computerized device with an associated display and input means that can interrogate the pacemaker and receive stored data as well as directly adjust the operating parameters of the pacemaker. The external device 300 shown in the figure may also be a remote monitoring unit. The external device 300 may also be interfaced to a patient management network 91 enabling the implantable device to transmit data and alarm messages to clinical personnel over the network as well as be programmed remotely. The network connection between the external device 300 and the patient management network 91 may be implemented by, for example, an internet connection, over a phone line, or via a cellular wireless link.

2. Delivery of Intermittent High-Energy Stimulation

As described above, high-energy electrical stimulation of the heart can be used to cause release of neurotransmitters in a way that mimics the beneficial effects of exercise. Chronic high-energy stimulation of the heart, however, would overstress the heart in HF patients and could be hazardous. Accordingly, such stimulation should be delivered on an intermittent basis. A device such as shown in FIGS. 1 and 2 can be configured to deliver intermittent high-energy cardiac stimulation by switching from a normal operating mode to a high-energy stimulation mode according to some defined schedule that specifies switching in response to lapsed time intervals and/or in response to one or more particular triggering events or conditions. If the device is configured to switch to the high-energy stimulation mode in response to a triggering event or condition, some limit could be imposed on the amount of stimulation delivered over a specified period of time. In the normal operating mode, the device may deliver no therapy at all or may be configured to delivery therapies such as bradycardia pacing, cardiac resynchronization pacing, and/or shocks or anti-tachycardia pacing in response to detection of tachyarrhythmias. After switching to the high-energy stimulation mode, the device may then deliver the high-energy stimulation in the form of excitatory pacing pulses to one or more myocardial sites, where the pacing pulse energy may be greater than that used for conventional pacing, and/or in the form of shocks with a shocking energy less than that used for cardioversion/defibrillation therapy. The high-energy stimulation mode may also allow therapies of the normal operating mode to continue such as bradycardia pacing, cardiac resynchronization pacing, and/or shocks or anti-tachycardia pacing in response to detection of tachyarrhythmias.

In order to provide intermittent high-energy stimulation, the device switches from its normal operating mode to the high-energy stimulation mode based upon lapsed time intervals and/or in response to detection of one or more particular triggering conditions or events. In another embodiment, the device may switch to the high-energy stimulation mode upon receiving a command to do so for some specified period of time, where such a command may be received from an external programmer, or received via a patient management network. A defined schedule may specify switching to the high-energy stimulation mode at periodic intervals (e.g., for five minutes each day) or at a random time during each day or other specified time period. Such a defined schedule could also specify a time for switching to the high-energy stimulation mode when a patient is expected to be awake or when a patient is expected to be sleeping. A defined schedule may also prescribe an amount of time over a specified time period for which the device is to operate in the high-energy stimulation mode. For example, the defined schedule may prescribe that high-energy stimulation be delivered for one hour each day. The controller may then programmed to opportunistically switch to the high-energy stimulation mode when one or more specified triggering conditions are met in order to meet the prescriptions of the defined schedule. Examples of possible triggering conditions are a measured exertion level being within a specified entry range, a measured heart rate being within a specified entry range, and actuation of a magnetically or tactilely actuated switch incorporated into the device by the patient that initiates high-energy stimulation. In such embodiments, the high-energy stimulation delivered in response to the triggering events may then be limited in amount or duration over some specified period of time. For example, the device could be programmed to deliver no more than 30 minutes of high-energy stimulation per day in response to such triggering events.

Figure 3:
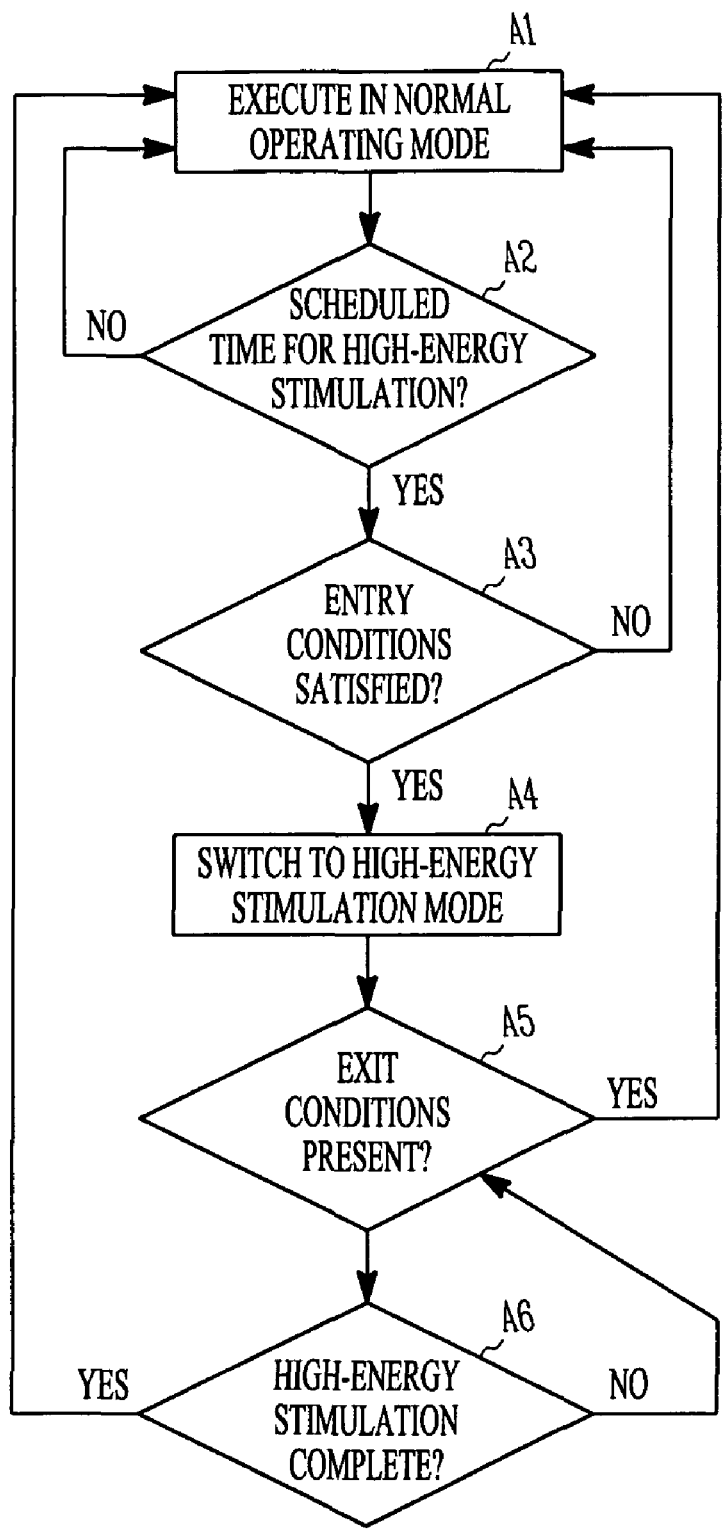
FIG. 3 illustrates an exemplary algorithm for implementing intermittent high-energy stimulation.

FIG. 3 illustrates one way that intermittent high-energy stimulation may be implemented by a cardiac device. In this embodiment, the controller of the device is programmed to transition through a number of different states, designated as A1 through A6. At state A1, the device operates in its normal operating mode. At state A2, while continuing to operate in state A1, the device determines whether it should switch to the high-energy stimulation mode based upon a lapsed time interval or a triggering condition. Optionally, the device may also be configured to test for one or more particular entry conditions before switching to the high-energy stimulation mode as implemented by state A3. Examples of entry conditions that must be satisfied before the switch to the high-energy stimulation mode include a measured exertion level being within a specified entry range, a measured heart rate being within a specified entry range, non-detection of cardiac arrhythmias, non-detection of cardiac ischemia, and actuation of a magnetically or tactilely actuated switch incorporated into the device by the patient that allows delivery of high-energy stimulation. At state A3, the device checks to see if the one or more entry conditions are satisfied and returns to state A1 if not. If the appropriate entry conditions are satisfied, the device switches to the high-energy stimulation mode at state A4. As discussed above, the high-energy stimulation mode supercedes the normal operating mode to the extent necessary to carry out the high-energy stimulation but may allow certain functions performed in the normal operating mode to continue. Alternatively, the high-energy stimulation mode could be said to incorporate particular functions of the normal operating mode, which functions are modified if necessary to deliver the high-energy stimulation. While executing in the high-energy stimulation mode, the device may optionally be configured to monitor for one or more exit conditions which cause the device to revert to the normal operating mode. Such exit conditions could be the same or different from the entry conditions that must be satisfied before entering the high-energy stimulation mode. At state A5, while executing in the high-energy stimulation mode, the device monitors for the occurrence of one or more exit conditions such as a measured exertion level being outside a specified permissible range, a measured heart rate being outside a specified permissible range, presence of a cardiac arrhythmia, presence of cardiac ischemia, and actuation of a magnetically or tactilely actuated switch incorporated into the device by the patient to stop delivery of high-energy stimulation. If an exit condition occurs, the device returns to the normal operating mode at state A1. Otherwise, the device proceeds to state A6 and checks to see if the prescribed amount and/or duration of high-energy stimulation has been delivered. If the specified amount or duration of high-energy stimulation has been delivered, the device returns to state A1 and resumes the normal operating mode. Otherwise, the device loops back to state A5 to monitor for exit conditions.

In one embodiment, the device is configured to deliver the high-energy stimulation in the form of excitatory pacing pulses where the pacing pulse energy is sufficient to cause local release of neurotransmitters. The minimum level of pacing pulse energy high enough to cause local release of neurotransmitters may vary with the particular patient as well as the type and placement of the stimulation electrode. Such a minimum level could be determined empirically but in any case would be higher than that used for conventional bradycardia or anti-tachycardia pacing. For example, while conventional pacing is performed using a pacing pulse amplitude of 0.5 to 1.0 volts and a pulse width of 0.5 to 2.0 milliseconds, high-energy stimulation pacing may, in one particular embodiment, use a pacing pulse amplitude on the order of 2.0 to 12 volts and a pacing pulse width of 2-20 milliseconds. Intermittent high-energy stimulation pacing may be delivered to the atria and/or ventricles as right ventricle-only, left ventricle-only, biventricular, or other multi-site pacing in any selected pacing mode such as DDD, VDD, or VVI. In the case where the normal operating mode includes delivery of some sort of pacing therapy, switching to high-energy stimulation mode may or may not include altering the pacing configuration and/or pacing mode from that used in the normal operating mode. The pacing configuration specifies a specific subset of the available electrodes to be used for delivering pacing pulses, and the pacing mode specifies the timing for delivering the pacing pulses. The pacing configuration is defined by the controller selecting particular pacing channels for use in outputting pacing pulses and by selecting particular electrodes for use by the channel with switch matrix 70. In order to avoid unwanted side effects such as pain or skeletal muscle stimulation, high-energy pacing pulses should preferably be delivered in a bipolar electrode-to-electrode configuration as opposed to a unipolar electrode-to-can configuration, where the two electrodes making up the bipolar configuration are closely spaced apart on either the same or different leads. For example, while pacing therapy may be delivered in the normal operating mode as right-ventricle only pacing, high-energy pacing pulses may be delivered in the high-energy stimulation mode as biventricular or other multi-site pacing. The pacing modes (e.g., DDD, DDI, VVI) may also be the same or different when switching from the normal operating mode to the high-energy stimulation mode.

In order to reliably provide high-energy stimulation pacing when switched to the high-energy stimulation mode, the device can be programmed with escape intervals during the high-energy stimulation mode to ensure frequent pacing. For example, the high-energy stimulation pacing may be delivered to the ventricles in an atrial triggered synchronous mode (e.g., DDD or VDD) with predefined atrio-ventricular (AV) and ventricular-ventricular (VV) escape intervals or in a non-atrial triggered ventricular pacing mode (e.g., VVI) with a pre-defined VV escape interval where the length of the escape intervals may be set to values which result in a high pacing frequency. It may be desirable, however, to incorporate additional steps into the algorithm before switching. For example, the escape intervals for the high-energy stimulation mode may be dynamically determined before the mode switch in order to ensure a high pacing frequency. In an embodiment where the high-energy stimulation mode is a non-atrial triggered pacing mode, the device may measure the patient's intrinsic heart rate before the mode switch and then set the VV escape interval so that the pacing rate for the high-energy stimulation pacing mode is slightly higher than the intrinsic rate. If the patient is receiving rate-adaptive ventricular pacing therapy in the normal operating mode, the VV escape interval for the high-energy stimulation pacing mode may be similarly modulated by an exertion level measurement. In an embodiment where the high-energy stimulation pacing is delivered in an atrial triggered pacing mode, the device may measure the patient's intrinsic AV interval before the mode switch (e.g., as an average over a number of cycles preceding the mode switch) so that the AV escape interval for delivering ventricular pacing can be set to pace the ventricles at a high frequency during the high-energy stimulation period.

In another embodiment, the device is configured to deliver the high-energy stimulation in the form of shocks through, for example, the shocking channel used to deliver cardioversion/defibrillation shocks. Such shocks may be delivered with a shocking energy less than that used for cardioversion/defibrillation so as not to result in any pain or discomfort to the patient. For example, whereas cardioversion/defibrillation shocks are typically delivered with an energy of 10-30 joules, shocks delivered in the high-energy stimulation mode may be delivered at an energy on the order of 0.5 joules. Similar to the situation discussed above with respect to high-energy pacing, it is preferable for the low-energy shocks delivered in the high-energy stimulation mode to be delivered with a bipolar shocking configuration in order to avoid pain and unwanted muscular or nerve stimulation. Rather than delivering the shock as a voltage interposed between a shocking electrode (e.g., a coil electrode) and the can, as is typically done to deliver a cardioversion/defibrillation shock, low-energy shocks in the high-energy stimulation mode are preferably delivered between two relatively closely spaced shocking electrodes on the same or different leads. In order to prevent the possibility of inducing an arrhythmia, such low-energy shocks may be delivered during the high-energy stimulation mode synchronously with detection of an R wave (i.e., a ventricular sense) in a manner similar to that used for cardioversion shocks. Alternatively, low-energy shocks could be delivered either in place of, or together with, a pacing pulse in accordance with a bradycardia pacing mode.

The high-energy stimulation discussed above, whether delivered in the form of high-energy pacing pulses or low-energy shocks, is excitatory stimulation that causes depolarization of the myocardium. That is, the high-energy stimulation is delivered either in accordance with a bradycardia pacing mode or in synchrony with a sensed R wave such that the stimulation is delivered at a time when the myocardium is non-refractory. It may also be desirable to deliver additional high-energy stimulation, either in the form of pacing pulses or shocks, while the myocardium is in a refractory state. Such refractory high-energy stimulation may result in additional release of neurotransmitters. Accordingly, the device controller may be programmed to deliver one or more non-excitatory stimulation pulses during a cardiac refractory period in the high-energy stimulation mode, where the non-excitatory stimulation pulses may be pacing or shock pulses with an energy sufficient to cause local release of neurotransmitters.

3. Detection of Triggering, Entry, and Exit Conditions

As discussed above, it may be desirable for the device to switch to the high-energy stimulation mode according to a defined schedule only if one or more specified entry conditions are satisfied. Whether or not entry conditions are employed, it may also be desirable for the device to exit the high-energy stimulation mode if one or more specified exit conditions occur. Finally, a defined schedule for switching to the high-energy stimulation may employ one or more specified triggering conditions that when satisfied cause the mode switch. Discussed below are examples of conditions that can be detected by appropriately configured implantable device and used as entry, exit, and/or triggering conditions.

One example of a triggering and/or entry condition is if the measured exertion level is within a specified range, where the exertion level may be measured, for example, as minute ventilation with a minute ventilation sensor, as an activity level with an accelerometer, or some combination of such measurements. Another example of a triggering and/or entry condition is if the patient's heart rate is within a specified range, where the heart rate is measured via a cardiac sensing channel. With some patients, it may be desirable for the high-energy stimulation mode to take place when the patient is not active as reflected by a measured exertion level and/or heart rate below a specified value. With other patients, on the other hand, it may be desirable to switch to the high-energy stimulation mode only when the patient is deemed to be active, as determined by an exertion level and/or heart rate above a specified value. A measured exertion level and/or heart rate either above or below a specified value may also be used as a triggering event to initiate the high-energy stimulation mode for some specified period of time. A measured exertion level or heart rate may also be used as an exit condition such that the device is programmed to revert from the high-energy stimulation mode back to the normal operating mode if the measured exertion level and/or heart rate falls outside of a specified permissible range.

It may also be desirable to inhibit a switch to the high-energy stimulation mode and/or revert to the normal operating mode if the patient is presently experiencing some degree of cardiac ischemia and/or a cardiac arrhythmia is detected. The device may be configured to detect cardiac ischemia from a morphology analysis of an electrogram collected during an intrinsic or a paced beat, the latter sometimes referred to as an evoked response. The electrogram for detection of ischemia is recorded from a sensing channel that senses the depolarization and repolarization of the myocardium during a cardiac cycle. The sensing channel used for this purpose may be a sensing channel used for detecting cardiac arrhythmias and/or intrinsic beats or may be a dedicated channel. In order to detect ischemic changes in an electrogram, it may be preferable to record the electrogram with a unipolar electrode that "sees" a larger volume of the myocardium as a wave of electrical activity spreads than a bipolar electrode. In order to detect an ischemic change, the electrogram can be compared with a reference electrogram to see if an increased current of injury is present. The comparison may involve, for example, cross-correlating the recorded and reference electrograms or comparing ST segment amplitudes, slopes, or integrations with reference values.

In order to detect whether the patient is experiencing cardiac ischemia during pacing, the controller is programmed to analyze the recorded electrogram of an evoked response and look for a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. A current of injury results in an abnormal change in the electrical potentials measured by either a surface electrocardiogram or an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered. In order to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller is programmed to detect ischemia by looking for an increased current of injury in the recorded electrogram as compared with the reference electrogram, where the latter may or may not exhibit a current of injury. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

If a change in a recorded electrogram indicative of ischemia is detected and/or a cardiac arrhythmia is detected, the controller may be programmed to inhibit switching to high-energy stimulation mode and/or programmed to revert back to the normal operating mode. Detection of cardiac ischemia or cardiac arrhythmias may also be logged as clinically significant events in the pacemaker's memory, where the event log and/or the recorded electrogram exhibiting the ischemia or arrhythmia may then be later downloaded to a clinician for analysis via an external programmer and/or a patient management network. Information derived from other analyses or other sensing modalities may also be used to more specifically detect cardiac ischemia. For example, dyspnea or other abnormal breathing patterns may be detected using a minute ventilation sensor by programming the controller to compare the transthoracic impedance signal from the sensor with a template representing the abnormal pattern.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
    a plurality of stimulation channels for delivering electrical stimulation to a plurality of ventricular sites;
    a controller programmed to operate the device in either a normal operating mode or a high-energy stimulation mode;
    wherein the controller is programmed to periodically switch from the normal operating mode to the high-energy stimulation mode according to a defined schedule;
    an exertion level sensor for measuring an exertion level;
    wherein the controller is programmed to switch to the high-energy stimulation mode only if the measured exertion level is below a predetermined threshold;
    wherein, in the normal operating mode, the controller is programmed to deliver pacing pulses in accordance with a programmed pacing mode to a single ventricular site; and,
    wherein, in the high-energy stimulation mode, the controller is programmed to deliver high-energy excitatory electrical stimulation to a plurality of ventricular sites as pacing pulses at an energy higher than the energy of the pacing pulses delivered in the normal operating mode.

2. The device of claim 1 wherein, in the high-energy stimulation mode, the controller is programmed to deliver pacing pulses with a pacing pulse amplitude on the order of 2-12 volts and a pacing pulse width on the order of 2-20 milliseconds.

3. The device of claim 1 wherein the pacing channels for delivering high-energy stimulation includes electrodes for bipolar stimulation.

4. The device of claim 1 wherein the controller is programmed to deliver one or more non-excitatory stimulation pulses during a cardiac refractory period in the high-energy stimulation mode and wherein the non-excitatory stimulation pulses have an energy sufficient to cause local release of neurotransmitters.

5. The device of claim 1 wherein the exertion level sensor is a minute ventilation sensor.

6. The device of claim 1 further comprising a sensing channel for sensing cardiac activity and wherein the controller is programmed to switch to the high-energy stimulation mode only if a measured heart rate is within a specified entry range.

7. The device of claim 6 wherein the controller is programmed to switch to the high-energy stimulation mode only if no cardiac arrhythmia is detected.

8. The device of claim 1 further comprising a sensing channel for sensing cardiac activity and wherein the controller is programmed to detect cardiac ischemia and to switch to the high-energy stimulation mode only if no cardiac ischemia is detected.

9. The device of claim 1 further comprising an exertion level sensor for measuring a patient's exertion level and wherein the controller is programmed to switch from the high-energy stimulation mode to the normal operating mode if the measured exertion level is within a specified exit range.

10. The device of claim 1 further comprising a sensing channel for sensing cardiac activity and wherein the controller is programmed to switch from the high-energy stimulation mode to the normal operating mode if a measured heart rate is within a specified exit range.

11. The device of claim 10 wherein the controller is programmed to switch from the high-energy stimulation mode to the normal operating mode if a cardiac arrhythmia is detected.

12. The device of claim 1 further comprising a sensing channel for sensing cardiac activity and wherein the controller is programmed to detect cardiac ischemia and to switch from the high-energy stimulation mode to the normal operating mode if cardiac ischemia is detected.

13. The device of claim 1 wherein the defined schedule specifies particular times of a day for switching to the high-energy stimulation mode.

14. The device of claim 1 wherein the defined schedule prescribes an amount of time over a specified time period for which the device is to operate in the high-energy stimulation mode and wherein the controller is programmed to opportunistically switch to the high-energy stimulation mode when one or more specified triggering conditions are met in order to meet the prescriptions of the defined schedule.

15. The device of claim 14 wherein the one or more specified triggering conditions include a measured exertion level being within a specified entry range.

16. The device of claim 14 further comprising a sensing channel and wherein the one or more specified triggering conditions include a measured heart rate being within a specified entry range.

17. The device of claim 14 further comprising a patient actuated switch and wherein the one or more specified triggering conditions include the switch being actuated.

18. The device of claim 1 wherein the stimulation channel for delivering high-energy stimulation is a pacing channel and further wherein the controller is programmed to deliver high-energy electrical stimulation as high-energy pacing pulses in accordance with a programmed pacing mode in the high-energy stimulation mode at an energy on the order of five times the energy of the pacing pulses delivered in the normal operating mode.

19. The device of claim 1 further comprising a patient actuated switch and wherein the controller is programmed to switch to normal operating mode from the high-energy stimulation mode if the switch is actuated.

20. A cardiac rhythm management device, comprising:
one or more sensing channels for sensing cardiac electrical activity;
one or more pacing channels for delivering pacing pulses to ventricular sites;
a shocking channel that includes a coil electrode for delivering shocks to a ventricular site;
an exertion level sensor for measuring an exertion level;
a controller programmed to operate the device in either a normal operating mode or a high-energy stimulation mode;
wherein the controller is programmed to deliver a defibrillation shock via the shocking channel in response to detection of ventricular fibrillation;
wherein the controller is programmed to periodically switch from the normal operating mode to the high-energy stimulation mode according to a defined schedule;
wherein the controller is programmed to switch to the high-energy stimulation mode only if the measured exertion level is below a predetermined threshold;
wherein, in the normal operating mode, the controller is programmed to deliver pacing pulses in accordance with a programmed pacing mode via the pacing channels; and,
wherein, in the high-energy stimulation mode, the controller is programmed to deliver low-energy shock pulses to a ventricular site at an energy lower than that used for defibrillation shocks.

21. The device of claim 20 wherein the energy of the low-energy shock pulses is on the order of 0.5 joules.

22. The device of claim 20 wherein the controller is programmed to deliver the low-energy shock pulses in accordance with a programmed pacing mode.

23. The device of claim 20 wherein the controller is programmed to deliver the low-energy shock pulses in accordance with a programmed pacing mode together with a pacing pulse.

24. The device of claim 20 wherein the controller is programmed to deliver the low-energy shock pulses in synchrony with sensed R waves.

25. A method, comprising:
in a normal operating mode, delivering pacing pulses in accordance with a programmed pacing mode to a single ventricular site;
in a high-energy stimulation mode, delivering high-energy excitatory electrical stimulation to a plurality of ventricular sites as pacing pulses at an energy higher than the energy of the pacing pulses delivered in the normal operating mode
periodically switching from the normal operating mode to the high-energy stimulation mode according to a defined schedule; and,
measuring an exertion level and switching to the high-energy stimulation mode only if the measured exertion level is below a predetermined threshold.

* * * * *